(12) United States Patent
Biehl et al.

(10) Patent No.: US 6,200,270 B1
(45) Date of Patent: Mar. 13, 2001

(54) SENSOR FOR NON-INVASIVE AND CONTINUOUS DETERMINATION OF THE DURATION OF ARTERIAL PULSE WAVES

(75) Inventors: Margit Biehl, St. Wendel; Stefan Kiefer, Merchweiler, both of (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 0 days.

(21) Appl. No.: 09/068,448

(22) PCT Filed: Oct. 23, 1996

(86) PCT No.: PCT/DE96/02010

§ 371 Date: May 8, 1998

§ 102(e) Date: May 8, 1998

(87) PCT Pub. No.: WO97/17016

PCT Pub. Date: May 15, 1997

(30) Foreign Application Priority Data

Nov. 10, 1995 (DE) .............................. 195 42 019

(51) Int. Cl.[7] ................................... A61N 5/00
(52) U.S. Cl. ..................... 600/493; 600/490; 73/753
(58) Field of Search .................... 600/481–483, 600/493, 500–504; 128/897–898

(56) References Cited

U.S. PATENT DOCUMENTS 4,245,648 * 1/1981 Trimmer et al. ................. 600/481
4,784,152 * 11/1988 Shinoda et al. .................. 600/481
5,533,511 * 7/1996 Kaspari et al. ................... 600/493
5,730,137 * 3/1998 Amano et al. ................... 600/485
5,830,131 * 11/1998 Caro et al. ....................... 600/493

FOREIGN PATENT DOCUMENTS 0 289 700  11/1988  (EP) .

OTHER PUBLICATIONS

Sensors and Actuators—A Physical A23 (1990) Apr., No.1/3 entitled "A Piezopolymer Finger Pulse and Breathing Wave Sensor", pp. 879–882.

* cited by examiner

Primary Examiner—John P. Lacyk
Assistant Examiner—Michael Astorino
(74) Attorney, Agent, or Firm—Staas & Halsey LLP

(57) ABSTRACT

A sensor for non-invasive and continuous determination of the duration of arterial pulse waves is provided in which at least two spaced apart piezoelectric pressure sensors are disposed in succession in the flow direction of the artery, with the sensor being provided with pressure sensitive surfaces and being integrated in a casing. The piezoelectric pressure sensors are provided with a pressure-sensitive, strip-shaped surface, with the strips each being disposed in their longitudinal extension perpendicular to the flow direction of the artery. The casing is provided with at least two recesses adapted to the contours of the strip-shaped surfaces into which the pressure-sensitive, strip-shaped surfaces of the pressure sensors are disposed flush to the surface of the casing.

16 Claims, 1 Drawing Sheet

SENSOR FOR NON-INVASIVE AND CONTINUOUS DETERMINATION OF THE DURATION OF ARTERIAL PULSE WAVES

BACKGROUND OF THE INVENTION

1. Field of the Invention

The present invention relates to a sensor for non-invasive and continuous determination of the duration of arterial pulse waves.

2. Description of the Related Art

A desirable goal for many manufacturers of blood-pressure measuring devices is continuous non-invasive measurement of human blood pressure without the aid of uncomfortable compression cuffs.

It has been known for quite some time that human blood pressure, differing from individual to individual, correlates to the velocity of pulse waves. Hitherto this fact could not be exploited for continuous measurement of blood pressure, because there are no reliable, inexpensive sensors available for determination of the pulse-wave velocity.

Hitherto, attempts have been made to determine the pulse-wave velocity, which is about 10 m/s at the wrist, via the change in the color, the form or in the electric resistance of the skin. Attempts have also been made to measure the pulse-wave velocity with the aid of the ultrasonic Doppler method, a reliable but not exactly inexpensive method. One such attempt is described in DE-OS-1 905 620. Two spaced apart piezoelectric oscillator systems, the conical-shaped sound of which irradiates a to-be-examined vessel and a Doppler reception device permit determination of the vessel-wall velocity with which the vessel wall is extended by the blood-pressure waves flowing through the vessel. Ultimately information on the pulse-wave velocity is obtained via a special evaluation algorithm.

Another example for determining the pulse-wave velocity is indicated in U.S. Pat. No. 4,245,648 describing a process and a device for measuring blood pressure and for determining the pulse rate. Two pressure-sensitive sensors housed in an arm cuff are placed along a blood-conducting vessel. The increase-in-pressure values determined in intervals can be utilized for calculating the pressure-wave velocity. However, disadvantageous is the large size of the device making it impossible to use at sites that are difficult to reach. Furthermore, application of the device involves considerable motoric impediment.

DESCRIPTION OF THE INVENTION

The object of the present invention is to further improve the sensor known from U.S. Pat. No. 4,245,648 in such a manner that it is designed so small and compact that it can be combined, by way of illustration, with a wristwatch.

The solution to the object of the present invention is set forth in claim 1. Advantageous embodiments are the subject matter of the subclaims.

An element of the present invention is that a sensor for non-invasive and continuous determination of the duration of arterial pulse waves, in which at least two piezoelectric pressure sensors are placed at intervals in succession in the running direction of the arteries, with the sensor being provided with pressure sensitive surfaces and integrated in a casing, is designed in such a manner that the piezoelectric pressure sensors have a pressure-sensitive, strip-shaped surface which are each placed in their longitudinal extension perpendicular to the running direction of the arteries, and that the casing is provided with at least two recesses adapted to the contours of the strip-shaped surfaces into which the pressure-sensitive, strip-shaped surfaces of the pressure sensors are disposed flush to the casing surface.

The invented sensor determines non-invasively the pressure pulsations of the arteria radialis preferably at the wrist level at two closely adjacent positions of which the one is located more proximally and the other more distally at the measuring point of the arteria radialis in the wrist region. The pulse-wave velocity and therefore, using previously patient related calibration, the average blood pressure can be determined from the time lag of the pulse maximum of the two measuring positions. The level of the systolic and diastolic pressure can be immediately determined from the measured difference between the pulse-pressure maximum and pulse-pressure minimum at one of the positions. The device is so small that it can be constantly worn on the wrist like a wristwatch, thereby largely avoiding any discomfort to the patient.

The sensor immediately determines the difference in the duration of the pulse wave propagating in the artery thereby setting stricter measurement criteria so that the invented sensor works more accurately than hitherto known measurement methods in which the indirect determination of the pulse wave occurs via the color, resistance, form of the skin. Inexpensive mass production of the sensor is also feasible.

For determination of the pressure, the invented sensor is provided with at least two separately operating pressure sensors which each are provided with a pressure-sensitive, strip-shaped surface and which are disposed in their longitudinal extension perpendicular to the running direction of the artery. The individual pressure sensors composed of piezoelectric material are integrated in a semi-cylindrical casing in such a manner that they are inserted in the angular running recesses in the casing wall at the convex, hemi-spherical nappe of the semi-cylinder.

Therefore, the individual pressure-sensitive surfaces essentially follow the convex-shaped hemispherical surface contour of the semi-cylinder which is pressed against the surface of the skin in such a manner that the curved pressure-sensitive surfaces intersect perpendicularly the running direction of the artery with radial polarization.

The purpose of the convex curvature of the semi-cylinder and the pressure sensitive surfaces connected thereto is to ensure, upon lightly pressing the sensor casing against the natural form of the surface of the skin, improved adaptation to the measuring site and therewith improved mechanical contacting of the measuring object. Furthermore, the purpose of the semi-cylindrical surface contour of the sensor casing is largely insensitive to overturning at the longitudinal axis.

Moreover, the pressure-sensitive surfaces of the pressure sensor has to be designed narrow in the direction of the running direction of the artery so that a small as possible duration of the pulse wave at each individual sensor area can be attained, thereby permitting obtaining high temporal resolution. The distance between the two pressure sensitive surface areas has to be selected so small that both pressure sensors still lie close to the surface in the region of the course of the arteria radialis. Only in this manner, can both pressure sensors detect the same temporal pulse duration. On the other hand, the distance has to be large enough in order to be able to still pick up the time lag of the pulse maximum between the two pressure sensors. Tests have shown that these conditions can be realized if the individual pressure-sensitive surfaces have a width of 1 mm and are spaced 1 cm apart.

The individual piezoelectric pressure sensors are composed of piezoelectric material and their surface facing the artery projects through the aforementioned recesses worked into the convex shaped casing wall. In this way. the individual piezo electric pressure sensors assume a hemispherical shape, in which upon external pressure polarization charges, which lead to an electric voltage between the pressure sensor surfaces, are released between their external and their internal surface proportional to the application of mechanical pressure or tension.

In view of the fact that when pressure is applied, a high voltage is generated between the surfaces of the piezoelectric pressure sensors by relatively small charges, low-frequency pressure fluctuations, such as arterial pressure pulsations, can no longer be detected if the receiver is directly connected to a low-ohmic signal processing system. Therefore a preamplifier with a high as possible input resistor and a low as possible output resistor is required which is placed as close as possible to the piezoelectric element.

Preferably, a simple, as small as possible to-be-realized impedance converter circuit, which by way of illustration is composed of a field effect transistor and two resistors, which are immediately integrated inside the sensor casing, should be provided for each piezoelectric pressure sensor. Due to its high-ohmic input, the entire sensor electronics should be completely screened off against electric interferences.

BRIEF DESCRIPTION OF THE DRAWING

The present invention is made more apparent in the following using preferred embodiments with reference to the drawings by way of example. Depicted is in.

DESCRIPTION OF THE PREFERRED EMBODIMENTS

Figure 1:
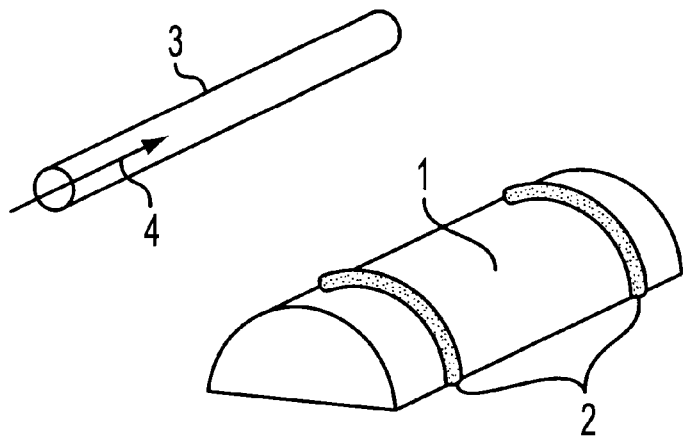
FIG. 1 an external view of an invented sensor.

FIG. 1 shows an invented preferred embodiment of a sensor for non-invasive and continuous determination of the duration of arterial pulse waves, which is provided with a semi-cylindrical casing 1. Two spaced apart piezoelectric pressure sensors 2 are worked into the hemispherical, convex outer contour of the casing. The invented sensor is pressed with its convex, hemispherical semi-cylindrical surface at the area of an artery 3 through which pulse waves 4 travel. The sensor casing 1 is preferably provided with a radius of curvature of 2.5 mm in the convex, hemispherical nappe area and of about 14 mm on the overall length of the casing. Preferably two angularly running recesses, through which piezoelectric pressure sensor materials 2 project through from the inside, are provided in the convex, hemispherical nappe area of casing 1.

Figure 2:
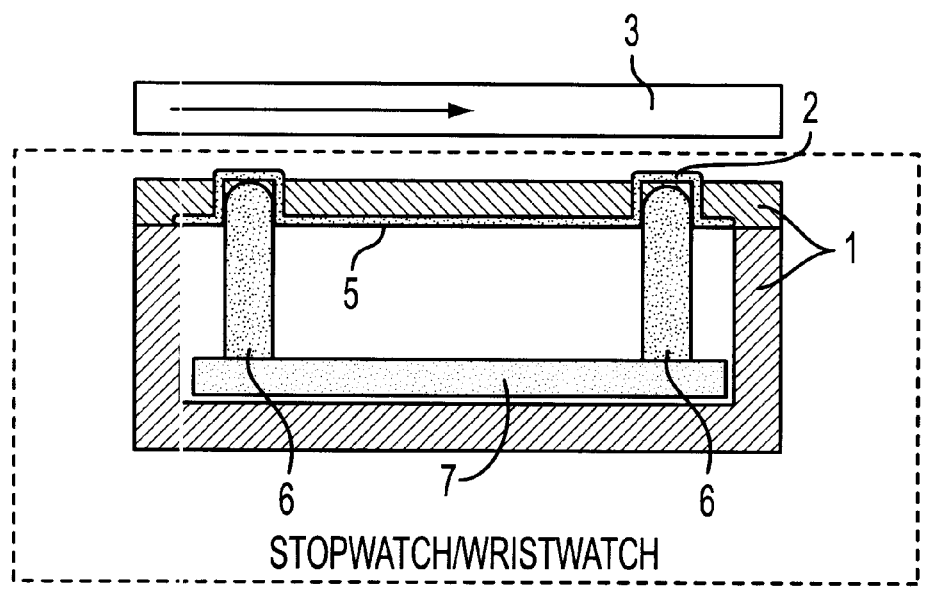
FIG. 2 a longitudinal section of an invented sensor.

FIG. 2 shows a longitudinal representation through an invented sensor, whose convex hemispherical nappe surface faces artery 3. As the representation shows. The top side of the semi-cylindrical casing 1 is interrupted by two recesses through which a piezoelectric sheeting 5 projects from the inside. The piezopolymer sheeting 5 slightly protrudes beyond the surface of casing 1. The outward facing pressure-sensitive surface of the sheeting is, in addition, metallized and thus in electrical contact with the metal sensor housing. Preferably the contacting occurs via a press contact or adhesion contacting.

In order to tap polarization charges generated on the bottom side of the sheeting due to the deformation of the piezopolymer sheeting, hemispheric disks of a conductive elastomer 6 are provided, which connect the piezopolymer sheeting to an impedance converter circuit which is placed on a substrate 7 for each individual pressure sensor. The voltage tapping at the internal side of each pressure sensor occurs in the area of the recesses via the respective conducting elastomer hemispheric disk 6 of approximately 1 mm thickness. The elastomer hemispheric disks 6 are contacted by means of press contacting to the non-metallized internal side of the piezo sheeting 5 with the respective signal input of both integrated impedance converter circuits on the substrate 7. Simultaneously, due to the elastic lining of the rear side of the sheeting by using elastic elastomer hemispheric disks ensures that the sheeting surface is pressed slightly outward at the recesses and therefore is essentially flush on the front to the surface of the casing or slightly raised.

Evaluation of the time lag of the pulse maxima occurs by means of differentiating the impedance converter/output signals. The time-lagged zero passes of the two differentiated pulse pressure courses can be utilized to start or stop an electronic stopwatch. The small size of the sensor could permit wearing the sensor on a wristband together with a miniaturized evaluation electronics including a display for showing the pulse frequency and blood pressure.

What is claimed is:

1. A sensor for non-invasive and continuous determination of a duration of arterial pulse waves of an artery, the sensor comprising:

at least two spaced apart piezoelectric pressure sensors, each of which is provided with a pressure-sensitive, strip-shaped surface;

a casing having at least two recesses adapted to contours of said strip-shaped surfaces, said pressure-sensitive, strip-shaped surfaces being integrated in said casing within said recesses so as to be disposed flush with an outer surface of said casing; and wherein said at least two spaced apart piezoelectric pressure sensors are disposed in succession in said casing such that said respective pressure sensors are arrangeable to extend longitudinally in a direction perpendicular to a flow direction of the artery.

2. The sensor according to claim 1, wherein said casing is metallic.

3. The sensor according to claim 1, wherein said pressure-sensitive, strip-shaped surfaces of said piezoelectric pressure sensors have a strip width which is smaller than a spacing between said piezoelectric pressure sensors.

4. The sensor according to claim 2, wherein said pressure-sensitive, strip-shaped surfaces of said piezoelectric pressure sensors have a strip width which is smaller than a spacing between said piezoelectric pressure sensors.

5. The sensor according to claim 3, wherein said space between said at least two piezoelectric pressure sensors is about 1 cm and said strip width is about 1 mm.

6. The sensor according to claim 4, wherein said space between said at least two piezoelectric pressure sensors is about 1 cm and said strip width is about 1 mm.

7. The sensor according to claim 2, wherein said casing has a semi-cylindrical shape, said recesses being provided in a convex hemispherical nappe of said casing such that said recesses run angularly at least partly about a cylindrical axis of said casing.

8. The sensor according to claim 7, wherein a radius of curvature of said semi-cylindrical shape is about 2.5 mm.

9. The sensor according to claim 1, wherein at least one of said two piezoelectric pressure sensors includes a piezopolymer sheeting in an area of said pressure-sensitive, strip-shaped surface.

10. The sensor according to claim 9, wherein said piezopolymer sheeting is a polyvinylidenefluoride having a metal coating at least on a side facing said casing in said area of said pressure-sensitive, strip-shaped surface.

11. The sensor according to claim 1, further comprising impedance converter circuits integrated within said casing and coupled to respective ones of said at least two piezoelectric pressure sensors for preamplifying piezoelectric signals from said pressure sensors.

12. The sensor according to claim 11, further comprising conductive elastic elements which respectively provide an electrical contact between an inside pressure sensitive surface of each of said piezoelectric pressure sensors and an associated one of said impedance converter circuits.

13. The sensor according to claim 12, wherein said conductive elastic elements are composed of conductive silicon rubber.

14. The sensor according to claim 1, further comprising one of a wristband and wristwatch in which said sensor is arranged, said one of said wristband and wristwatch being configured to allow for pulse frequency and blood pressure measurement of the artery when used.

15. The sensor according to claim 1, wherein in order to determine an interval of a pulse wave maxima in an arteria radialis of the artery, an interval between zero crossings of a first temporal derivation of sensor signals from said two spaced apart piezoelectric pressure sensors is registered.

16. The sensor according to claim 1, wherein said casing has a semi-cylindrical shape.

* * * * *